(12) United States Patent
Shirley et al.

(10) Patent No.: US 6,485,736 B1
(45) Date of Patent: Nov. 26, 2002

(54) VARIABLE RELEASE MICROCAPSULES

(75) Inventors: Ian Malcolm Shirley, Binfield (GB); Juanita Elena Van Koppenhagen, Vallejo, CA (US); Herbert Benson Scher, Moraga, CA (US); Richard Follows, Greater Manchester (GB); Philip Wade, Cheshire (GB); Fergus Gerard Paul Earley, Highfield (GB); Dianne Beth Shirley, Binfield (GB)

(73) Assignee: Syngenta Ltd., Surrey (GB)

( * ) Notice: Subject to any disclaimer, the term of this patent is extended or adjusted under 35 U.S.C. 154(b) by 0 days.

(21) Appl. No.: 09/656,718

(22) Filed: Sep. 7, 2000

(51) Int. Cl.[7] ................. A61F 13/00; A01N 25/28; A01N 25/32; B01J 13/02
(52) U.S. Cl. ............... 424/424; 504/359; 504/108; 427/213.3
(58) Field of Search ............... 427/213.3; 504/359, 504/108; 424/424

(56) References Cited

U.S. PATENT DOCUMENTS

| 4,180,064 A | * 12/1979 | Heller et al. ............. 427/213.3 |
| 4,285,720 A | 8/1981 | Scher et al. |
| 4,956,129 A | 9/1990 | Scher et al. |
| 5,160,529 A | 11/1992 | Scher et al. |
| 5,332,584 A | 7/1994 | Scher et al. |
| 5,997,946 A | * 12/1999 | Bell et al. ................ 427/213.3 |

* cited by examiner

Primary Examiner—Jose' G. Dees
Assistant Examiner—Robert M DeWitty
(74) Attorney, Agent, or Firm—Hale and Dorr LLP

(57) ABSTRACT

A novel microcapsule comprising a liquid core material which is substantially insoluble in water and enclosed within a solid permeable shell of a polymer resin containing disulfide linkages is disclosed. The process for producing such microcapsules is likewise disclosed.

11 Claims, 1 Drawing Sheet

US 6,485,736 B1

VARIABLE RELEASE MICROCAPSULES

FIELD OF THE INVENTION

This invention relates to microcapsules and to a process for their production. More particularly, this invention relates to encapsulated droplets of a liquid material which is substantially insoluble in water, wherein the encapsulating agent is a shell wall containing disulfide units, thereby forming an environmentally sensitive, variable release wall. Further, this invention relates to the processes for the production of such microcapsules and methods for their use.

BACKGROUND OF THE INVENTION

The use of microcapsules for the slow or controlled release of liquid, solid and solids dissolved or suspended in solvent is well known in the chemical art, including the pharmaceutical, specialty chemical and agricultural industry. In agriculture, controlled-release techniques have improved the efficiency of herbicides, insecticides, fungicides, bactericides and fertilizers. Non-agricultural uses have included encapsulated dyes, inks, pharmaceuticals, flavoring agents and fragrances.

The wall of the microcapsule are typically porous in nature, releasing the entrapped material to the surrounding medium at a slow or controlled rate by diffusion through the pores of the wall. In addition to providing controlled release, the walls also serve to facilitate the dispersion of water-immiscible liquids into water and water-containing media such as wet soil. Droplets encapsulated in this manner are particularly useful in agriculture, where water from irrigation, rain and water sprays is frequently present.

Various processes for microencapsulating material have been previously developed. These processes can be divided into three categories-physical methods, phase separation and interfacial reaction. In the physical methods category, microcapsule wall material and core particles are physically brought together and the wall material flows around the core particle to form the microcapsule. In the phase separation category, microcapsules are formed by emulsifying or dispersing the core material in an immiscible continuous phase in which the wall material is dissolved and caused to physically separate from the continuous phase, such as by coacervation, and deposit around the core particles. In the interfacial reaction category, microcapsules are formed by emulsifying or dispersing the core material in an immiscible continuous phase and then an interfacial polymerization reaction is caused to take place at the surface of the core particles.

The above processes vary in utility. Physical methods such as spray drying, spray chilling and humidized bed spray coating, have limited utility for the microencapsulation of products because of volatility losses and pollution control problems associated with evaporation of solvent or cooling, and because under most conditions not all of the product is encapsulated nor do all of the polymer particles contain product cores. Phase separation techniques suffer from process control and product loading limitations. It may be difficult to achieve reproducible phase separation conditions, and it is difficult to assure that the phase separated polymer will preferentially wet the core droplets.

Interfacial polymerization reaction methods have proven to be the most suitable processes for use in the agricultural industry for the microencapsulation of pesticides. There are various types of interfacial reaction techniques. In one type, the interfacial condensation polymerization microencapsulation process, two different monomers are brought together at the oil/water interface where they react by condensation to form the microcapsule wall.

In another type, the in situ interfacial condensation polymerization reaction, an organic phase which contains an oil core and one or more prepolymers is prepared. It is then dispersed into a continuous or aqueous phase solution comprising water and a surface-active agent. The organic phase is dispersed as discrete droplets throughout the aqueous phase by means of emulsification, with an interface between the discrete organic phase droplets and the surrounding continuous aqueous phase solution being formed. In situ self-condensation at the interface and curing of the polymers in the organic phase droplets is initiated by heating the emulsion to a temperature between about 20° C. to about 100° C. The heating occurs for a sufficient period of time to allow substantial completion of in situ condensation of the prepolymers to convert the organic droplets to capsules consisting of solid permeable polymer shells enclosing the organic core materials. Depending upon the type of prepolymer used, an acidifying agent may be required in order to maintain the pH of the emulsion at a range of about 0 to about 4 pH during condensation.

Two types of microcapsules prepared by in situ condensation are found in the art. One type, as exemplified in U.S. Pat. No. 4,285,720, is a polyurea microcapsule which involves the use of at least one polyisocyanate such as polymethylene polyphenylisocyanate (PMPPI) and/or tolylene diisocyanate (TDI) as the prepolymer. In the creation of polyurea microcapsules, the wall-forming reaction is initiated by heating the emulsion to an elevated temperature at which point the isocyanate polymers are hydrolyzed at the interface to form amines, which in turn react with unhydrolyzed polymers to form the polyurea microcapsule wall.

Another type, exemplified in U.S. Pat. Nos. 4,956,129, 5,160,529 and 5,332,584, incorporated herein by reference, is an aminoplast microcapsule wherein the wall-forming prepolymer is an etherified or alkylated amino formaldehyde (aminoplast) resin. The aminoplast microcapsule walls are formed by heating the emulsion while simultaneously adding to the emulsion an acidifying agent in order to maintain the emulsion pH at from about 0 to about 4 pH. The heating and lowering of the pH of the emulsion is maintained for a sufficient amount of time to allow in situ self-condensation and/or cross-linking of the amino resin thereby forming the aminoplast microcapsule wall.

Microcapsules produced by in situ condensation have the benefits of high pesticide loading and low manufacturing costs, as well as a very efficient membrane and no monomer residue remaining in the aqueous phase. Further, such microcapsules are capable of effecting a slow or controlled rate of release of the encapsulated material by its diffusion through the microcapsule shell to the surrounding medium.

These controlled release microcapsules provide longer term efficacy as the encapsulated material is released over a period of time and is available throughout the effective period. In the field of agriculture, this is particularly significant for pesticides or other ingredients which are degraded or decomposed over a relatively short period of time under certain environmental conditions. Use of microencapsulated compositions in these situations provides effective activity of the encapsulated ingredient over a longer period of time, typically several weeks, since it is released into the environment continuously in the amount needed rather than in one large initial dose. Controlled release microencapsulated pesticides are primarily used as preemergence pesticides wherein they are applied to the soil prior to the emergence of vegetation or appearance of insects. By such application, they are available over a period of time to kill or control newly emerged weed species or insects in their larval stages. Microencapsulated insecticides and fungicides can also be used for foliar application.

Microencapsulation of products such as pesticides provide the added benefit of increase in the safety of pesticide handling in that the polymer wall of the microcapsule minimizes the contact by the handler with the active pesticide. Still, there are instances where it is desirable to have the benefits of both the controlled gradual release and quick release of the encapsulated ingredient. Such an instance would be where the microcapsule is ingested by a harmful insect. In such a case, it would be desirable for the microcapsule wall to quickly break down, allowing a fast release of the pesticide into the insect gut. Further, in the instance where the microcapsule is ingested by a beneficial or non-harmful insect, it would be desirable that the microcapsule wall not break down, allowing the insect to survive.

SUMMARY OF THE INVENTION

It has been discovered that the wall of microcapsules formed by in situ condensation polymerization reaction similar to that described in U.S. Pat. Nos. 4,956,129, 5,160,529 and 5,332,584 can be modified by the inclusion of disulfide links in the aminoplast wall, or by replacement of the amino resin with compounds capable of forming or having disulfide links. These links serve to enhance the properties of the microcapsule wall such that the material contained within are released either by gradual controlled release or fast triggered release depending upon the environment in which the microcapsule is found.

Those environments include, for agricultural applications, the terrain or vegetation where such microcapsules may be applied. In such an environment, the encapsulated material would be released gradually. The environment may also include the gut of an insect, wherein conditions therein would trigger or cause the disulfide links to cleave, thereby allowing a quick or fast release of the encapsulated material. Accordingly, the encapsulated material may be gradually released across the wall of the microcapsule in an environment that does not induce cleavage of the disulfide links, or the disulfide links may cleave due to conditions in the environment surrounding the microcapsule thereby quickly releasing the encapsulated material.

The process for preparing such microcapsules comprises:

(a) preparing an organic solution or oil phase comprising the material to be encapsulated and the wall-forming material, whereby the wall-forming material is dissolved in the organic phase and comprises one or more cross-linking agents, in which at least one of the cross-linking agents is a polythiol compound and, optionally, an alkylated amino-formaldehyde prepolymer;

(b) creating an emulsion of the organic solution in a continuous phase aqueous solution comprising water, a protective colloid and, optionally, a phase transfer catalyst and/or emulsifier, wherein, the emulsion comprises discrete droplets of the organic solution dispersed throughout the continuous phase aqueous solution, with an interface formed between the discrete droplets of organic solution and the aqueous solution; and (c) causing in situ condensation and/or formation of disulfide linkages and curing of the wall-forming material in the organic solution of the discrete droplets at the interface with the aqueous solution by heating the emulsion and, optionally, simultaneously adding to the emulsion an acidifying agent whereby the pH of the emulsion is maintained between about 0 and about 4 for a sufficient period of time to allow substantial completion of wall formation, thereby converting the organic solution droplets to capsules consisting of solid permeable polymer shells enclosing the material.

Microcapsules formed by this process are capable of effecting a gradual controlled rate of release of the encapsulated material by diffusion through the shell to the surrounding medium. Further, microcapsules formed by this process are capable of effecting a fast rate of release of the encapsulated material by cleavage of the disulfide linkages in the presence of a surrounding medium which would promote such cleavage. The present invention resides in both the process described above and the microcapsules thus formed.

The release rate by Fickian diffusion of an active ingredient from a microcapsule may be defined by the equation:

$$\text{release\_rate} = \frac{(4\pi r'r'')P(c'-c'')}{r''-r'}$$

where $(4\pi r'r'')$ is the surface area of the capsule, P is the permeability of the wall, $r''-r'$ is the wall thickness, and $c'-c''$ is the concentration difference across the wall. The permeability P is the product of the diffusion (D) and partition (K) coefficients of the active ingredient and is largely dependent upon the chemical nature of the wall materials.

Release rates can be appreciably varied by altering the chemical composition and thus the permeability of microcapsule walls. The introduction of disulfide links offers one such approach. Moreover, disulfide linkages are susceptible to cleavage by several agents thereby enabling the possibility of triggered fast release upon demand. Possible triggering agents include base and/or reductive systems.

One aspect of this invention describes microcapsule wall compositions containing disulfide units and providing a semi-permeable barrier. The walls may be made from materials where (1) all the wall forming materials contain sulfur atoms; or (2) some of the wall forming materials contain sulfur atoms and some do not.

Another aspect of this invention describes a process for the introduction of disulfide bonds into microcapsule walls from materials where the disulfide unit (1) is generated during wall formation; or (2) is already present in the starting materials. The first option is preferred when the materials for wall formation are readily available and do not require special preparation in a separate step.

DETAILED DESCRIPTION OF THE INVENTION

Figure 1:
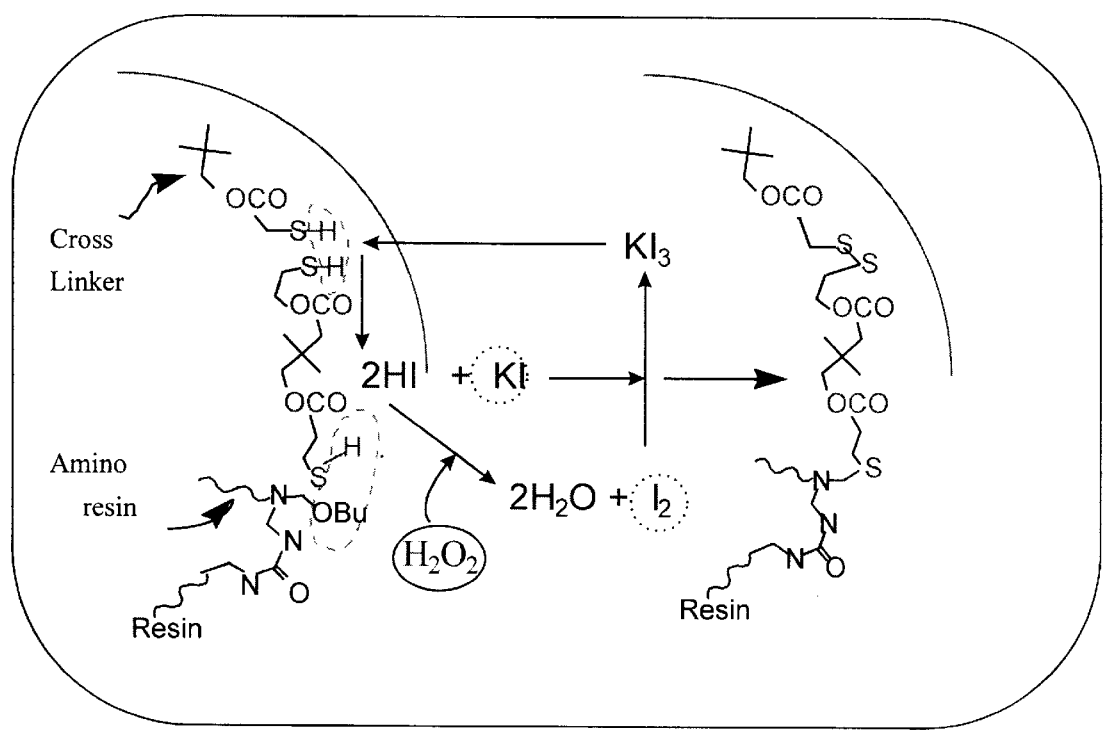
FIG. 1 generally illustrates catalytic synthesis of the disulfide linkages at the organic/aqueous interface.

It has been found that, by changing the method for wall formation in the above mentioned aminoplast microcapsule process, it is possible to produce a modified chemical structure which alters the properties of the wall. The process employs polythiol compounds and involves the sequential or simultaneous formation of disulfide links between some of the thiol groups of the cross-linking agent, and, when an aminoplast resin is utilized, the formation of thioether links between other thiol groups and the alkylated amino formaldehyde resin in the manner described above.

In its simplest form, the microcapsule of the present invention is comprised of a core material encapsulated by a wall formed from polythiol compounds, wherein the wall is comprised of disulfide links capable of "cleaving" in order to effect a quick release of the encapsulated material. Cleaving refers to the reaction in which the disulfide link is broken apart in order to release the core material.

The core material is typically a liquid and, in the case of agricultural products, may be comprised of one or more pesticides, or, in the case of non-agricultural products, may be comprised of inks, dyes, pharmaceuticals or other products. For agricultural products, the core may be an organic solution, typically immiscible with water, comprising one or more pesticides as the active ingredient, including insecticides, herbicides, fungicides and biocides. The pesticide may be a liquid, a solid pesticide which has been dissolved in a solvent which is immiscible with water, or a solid suspended in the organic solution which may have within it another pesticide. The organic solution may also have an ultraviolet protectant suspended or dissolved within it.

Capsule suspensions of the present invention may also be produced containing two materials which may be incompatible with each other, with one material encapsulated and the other contained in the aqueous phase of the suspension. Such combination products are storage stable and enable the production of a combination pesticidal product wherein incompatible pesticides may be applied together.

The materials utilized in forming the wall of the microcapsule are comprised of one or more polythiol compounds, wherein two moles of thiol are coupled together to form a disulfide link. The chemistry of wall formation is complex. In the process where the wall materials include an aminoplast resin, it is believed that the cross-linking condensation reaction between the aminoplast resin and the polythiol compound involves displacement of the alkoxy or methylol group by the thiol group to form a thioether linkage:

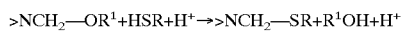

where $R^1$ represents a butylated (Bu) or methylol (H) functional group of a multi-functional aminoplast resin, and R represents a moiety bearing two or more thiol groups. For example, when pentaerythritol tetra-(3-mercaptopropionate) is used as the cross-linking agent, the cross-linked structure may be represented as:

where the cross-link is the —CH$_2$—S—CH$_2$— thioether group. The condensation reaction may be accelerated by acids and results in the formation of a thermoset polymer of theoretically infinite molecular weight.

Disulfide linkages are readily made from polythiol compounds by oxidation of the compounds. Oxidation and reduction always occur together in redox reactions where the electrons supplied by the reducing agent are accepted by the oxidizing agent. Thiols act as reducing agents in the reaction where two moles of thiol are coupled to form a disulfide group and generate two protons and two electrons:

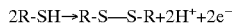

Under appropriate conditions the disulfide group may undergo further oxidation.

The generation of protons is of particular relevance when disulfide groups are made during wall formation of the above mentioned aminoplast wall systems. This is because the reduction in pH will simultaneously promote the formation of thioether linkages between other thiol groups and the alkylated aminoplast resin.

The Sulfur-Containing Wall Forming Precursors.

As mentioned above, the walls of the microcapsule of the present invention may be made from materials where all the wall forming materials contain sulfur atoms, or some of the wall forming materials contain sulfur atoms and some do not. Further, with respect to the disulfide links, those links may be already present or pre-prepared in the starting materials used to form the wall, or the links may be generated during wall formation.

In one embodiment of the present invention, the instance where all of the wall forming materials contain sulfur atoms, one or more polythiol compounds are used to form disulfide bonds during microcapsule wall formation in the absence of an alkylated amino formaldehyde resin. It will be appreciated by those skilled in the art that the robustness of the wall will depend upon the number of disulfide links made and the molecular weight of the polythiol compound(s). Examples of suitable thiol compounds include, inter alia, pentaerythritol tetra-(3-mercaptopropionate) and pentaerythritol tetrathioglycolate.

In another embodiment of the present invention, where some of the wall forming materials contain sulfur atoms and some do not, an alkylated amino formaldehyde resin and a compound already containing a disulfide link are used to form microcapsule walls. It is preferred that the compound already containing the disulfide link is substantially soluble in the organic phase. Cross-linking or self-condensation of aminoplast resins may also be effected through functional groups other than thiols, such as alcohols or amines. An example of a suitable disulfide compound includes, inter alia, 2-hydroxyethyl disulfide. Also suitable are molecules made by the oxidative coupling of 3-mercapto-1,2-propanediol:

[HOCH$_2$CHOHCH$_2$—S—S—CH$_2$CHOHCH$_2$OH]

It will be appreciated by those skilled in the art that the alcohol groups of this molecule may be esterified with thiol-containing carboxylic acids in the same manner as described above to give structures having increased oil solubility:

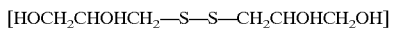

where Z is hydrocarbyl or aryl-hydrocarbyl.

In a preferred embodiment of this invention, a polythiol compound is mixed with an alkylated amino formaldehyde resin, and the disulfide bonds and thioether bonds described above are formed during microcapsule wall formation. While molecules having two thiol groups are suitable, preferably the polythiol compound has more than two thiol groups. Other functional groups within the polythiol compound are acceptable provided that they are substantially soluble in the organic phase and do not adversely affect wall formation. Examples of compounds having two thiol groups include, inter alia, 1,4-butanedithiol, 1,5-pentanedithiol, 1,6-hexanedithiol, 1,8-octanedithiol and xylene-α,α'-dithiol.

Preferred polythiol compounds for use in this invention can be made by reaction of a multifunctional alcohol with a thiol-containing carboxylic acid derivative HS-Z-CO$_2$R' to give thiol-containing esters:

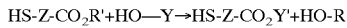

where R' is H or alkyl or aryl, Z is hydrocarbyl or aryl-hydrocarbyl, and Y is a hydrocarbyl unit containing two or more hydroxyl groups. Examples of multifunctional alcohols include, inter alia, ethylene glycol, polyethylene glycols, glycerol, trimethylolpropane, pentaerythritol, dipentaerythritol and 1,2,6-hexantriol. Examples of the thiol-containing carboxylic acid derivative $HS-Z-CO_2R'$ include 3-mercaptopropionic acid, thioglycolic acid, thiolactic acid, methyl 3-mercaptopropionate, methyl thioglycolate, and methyl thiolactate.

Instead of preparing the esters by reacting the alcohol with the carboxylic acid derivative, a number of suitable esters are available commercially, including, inter alia, 1,2,6-hexanetriol trithioglycolate from Aldrich; 1,2,3-propanetriol trithioglycolate from Bruno; trimethylolpropane tris(2-mercaptoacetate) from Aldrich, ICN-RF, Salor, Pfaltz and Bauer and Bruno; trimethylolpropane tris(3-mercaptopropionate) from Aldrich, Pfaltz & Bauer and Bruno; pentaerythritol tetra-(3-mercaptopropionate) from Aldrich, Bruno, Fluka, ICN-RF, Salor, Pfaltz & Bauer and TCI-US; and pentaerythritol tetra-(2-mercaptoacetate) from Aldrich, Bruno, Salor and TCI-US. Particularly preferred esters are those made from glycerol, or trimethylolpropane or pentaerythritol and 3-mercaptopropionic acid or thioglycolic acid. Such esters are usually readily soluble in a range of oils relevant for the delivery of agrochemicals.

Suitable thiol compounds for use in this invention can also be made by reaction of a multifunctional amine molecule with a thiol-containing carboxylic acid derivative $HS-Z-CO_2R'$ to give thiol-containing amides

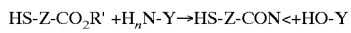

where R' is H or alkyl or aryl, Z is hydrocarbyl or arylhydrocarbyl, and Y is a hydrocarbyl unit containing two or more amine groups or one amine group and one or more alcohol groups, and n is 1 or 2. Although generally less soluble in oils relevant for the delivery of agrochemicals than the above mentioned esters, polyamide-thiol compounds may also be used in the encapsulation process. Examples of the thiol-containing carboxylic acid derivative $HS-Z-CO_2R'$ include 3-mercaptopropionic acid, thioglycolic acid, thiolactic acid, methyl 3-mercaptopropionate, methyl thioglycolate and methyl thiolactate. Examples of amine-containing compounds include, inter alia, di-, tri- and pentaethylenediamine, 1,4-diaminobutane, 1,6-diaminohexane, $C_2H_5C[CH_2O(CH_2CHMe)_{1.7-2}NH_2]_3$ (commercially available as Jeffamine® T-403 from Huntsman), and 3-amino-1,2-propanediol.

Although polythiol compounds are preferred, compounds that contain both thiol groups capable of forming disulfide bonds and other functional groups such as alcohol or amines capable of reacting with alkylated amino formaldehyde resins can also be utilized. In this instance, wall forming conditions would be selected such that disulfide bonds were formed before cross-linking with the resin. Examples of compounds having two thiol groups and alcohol groups capable of reacting with the alkylated amino formaldehyde resin include, inter alia, 2,3-dimercapto-1-propanol and 1,4-dimercapto-2,3-butanediol.

The Resin.

In compositions where some of the wall forming materials contain sulfur atoms and some do not, the materials without sulfur atoms are partially etherified amino formaldehyde resin prepolymers with high solubility in the organic phase and low solubility in the aqueous phase. In the non-etherified form, the prepolymer contains a large number of methylol groups in its molecular structure. Etherified prepolymers have the hydroxyl group hydrogen atoms replaced by alkyl groups, and are obtained by condensation of a compound containing amino groups with formaldehyde and an alcohol.

The prepolymers should be soluble in the organic phase. Preferably, the alkyl groups have four or more carbon atoms and more than about 50% of the hydroxyl hydrogen atoms on the prepolymer molecule have been replaced. Those useful in the above process are those in which about 50% to 90% of the hydroxyl hydrogen atoms have been replaced by alkyl groups, as some hydroxyl groups are needed for the condensation/polymerization which occurs in the wall forming step. Most preferably, about 70% to 90% of the methylol groups have been etherified with a $C_4$–$C_6$ alcohol. The alcohol may be straight chained or branched.

The aminoplast resin may be one of four general types: urea formaldehyde, melamine formaldehyde, benzoguanamine formaldehyde and glycoluril formaldehyde. The first two mentioned are preferred, with urea formaldehyde prepolymers being most preferred. The prepolymers utilized may be commercially available etherified resin prepolymers. Some commercially available prepolymers are those sold by Cytec under the trade names Beetle® and Cymel®, the Beckamine® line sold by Reichhold Chemicals, and the Resimen® line sold by Solutia.

The Oxidant.

Numerous oxidation reagents are known. The following illustrates a selection of oxidants which may be suitable for forming disulfides from thiols ($2R-SH \rightarrow R-SS-R+2H^++2e^-$) either during in situ interfacial polymerization or prior to adding to the organic phase:

Halogen Elements (in water):

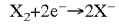

where X is Cl, Br or I

Potassium Permanganate (in acidic solution):

$$MnO_4^-+8H^++5e^- \rightarrow Mn^{2+}+4H_2O$$

Potassium Dichromate (in acidic solution):

$$Cr_2O_7^{2-}+14H^++6e^- \rightarrow 2Cr^{3+}+7H_2O$$

Ferric Salts (in solution):

$$Fe^{3+}+e^- \rightarrow Fe^{2+}$$

Hydrogen Peroxide (in aqueous solution):

$$H_2O_2+2H^++2e^- \rightarrow 2H_2O$$

The extent to which redox reactions will occur is largely determined by how readily the reagents will respectively give up and accept electrons. Quantitative aspects of oxidation and reduction may be predicted by reference to the value of the redox potential of a given reagent. A selection of redox potentials for various systems is illustrated below:

TABLE 1

Redox Potentials for Various Systems

| system | | redox potential volts |
|---|---|---|
| $H_2$ | $\rightarrow 2H^+ + 2e^-$ | 0 |
| $H_2S$ | $\rightarrow 2H^- + S + 2e^-$ | +0.14 |
| $Fe(CN)_6^{4-}$ | $\rightarrow Fe(CN)_6^{3-} + e^-$ | +0.36 |
| $2I^-$ | $\rightarrow I_2 + 2e^-$ | +0.53 |
| $3I^-$ | $\rightarrow I_3^- + 2e^-$ | +0.54 |
| $2H_2SO_3$ | $\rightarrow S_2O_6^{2-} + 4H^- + 2e^-$ | +0.56 |
| $H_2O_2$ | $\rightarrow O_2 + 2H^+ + 2e^-$ | +0.70 |
| $Fe^{2+}$ | $\rightarrow Fe^{3+} + e^-$ | +0.77 |
| $2HNO_2$ | $\rightarrow N_2O_4 + 2H^- + 2e^-$ | +1.07 |

TABLE 1-continued

Redox Potentials for Various Systems

| system | | | redox potential volts |
|---|---|---|---|
| $2Br^-$ | $\rightarrow$ | $Br_{2(aq)} + 2e^-$ | +1.10 |
| $Cr_2O_7^{2-} + 14H^- + 6e^-$ | $\rightarrow$ | $2Cr^{3-} + 7H_2O$ | +1.23 |
| $2Cl^-$ | $\rightarrow$ | $Cl_2 + 2e^-$ | +1.36 |
| $H_2O_2$ | $\rightarrow$ | $HO_2 + H^- + e^-$ | +1.50 |
| $4H_2O + Mn^{2+}$ | $\rightarrow$ | $MnO^{4-} + 8H^- + 5e^-$ | +1.52 |
| $MnO_2 + 2H_2O$ | $\rightarrow$ | $MnO^{4-} + 4H^- + 3e^-$ | +1.68 |
| $2H_2O$ | $\rightarrow$ | $H_2O_2 + 2H^- + 2e^-$ | +1.78 |
| $2F^-$ | $\rightarrow$ | $F_2 + 2e^-$ | +2.87 |

The lower the system appears in the redox series as written above, the more powerful the oxidizing tendency of the oxidizing agent, i.e., the system on the right hand side of the arrow. To illustrate, iodine can oxidize hydrogen sulfide to sulfur but cannot oxidize chloride ion to chlorine.

Redox potentials for a selection of thiol to disulfide reactions (2RSH→R-SS-R) taken from the literature are tabulated below:

TABLE 2

Redox Potentials for Thiol to Disulfide Reactions

| Thiol | redox potential volts | Reference |
|---|---|---|
| $C_2H_5SH$ | +0.41 | 1 |
| $n-C_6H_{13}SH$ | +0.36 | 1 |
| $n-C_{12}H_{25}SH$ | +0.33 | 1 |
| $C_6H_5SH$ | +0.18 | 1 |
| $SHCHCH_3CO_2H$ | +0.08 | 2 |
| $HSCH_2CH(NH_2)CO_2H$ | -0.10 | 3 |
| | +0.08 | 4 |
| $HOCH_2CH_2SH$ | +0.44 | 5 |
| $HO_2CCH_2SH$ | +0.42 | 5 |

References

1. R. Geyer & K. G. Hausler, 64 *Acta Chim. Acad. Scien. Hung, Tomus* (1970) pp. 365–68.
2. H. Borsook, E. L. Ellis & H. M. Huffman, 117 *J. Biol. Chem.*, (1937) pp. 281–308.
3. Fa Zhang, & G Dryhurst, 37 *J. Med. Chem.*, (1994) 8, pp. 1084–98.
4. I. M. Kolthoff, W. Stricks & R. C. Kapoor, 77 *J. Amer. Chem. Soc.*, (1955) pp. 4733–39.
5. E. K. Fisher, 89 *J. Biol. Chem.*, (1930) pp.753–63.

The value of the redox potential is sensitive to structure. The thiol structures illustrated above have values less than +0.5 volts. Oxidation reagents with a higher redox value will promote the oxidative coupling of such thiols. All reagents in the above Table 1 from iodine down are suitable for such reactions.

The stoichiometry of the reaction is controlled by the ratio of the reagents affording electrical neutrality. To illustrate, redox reactions for the oxidative coupling of thiols are written for iodine (0.54V), ferric ion (0.77V), oxygen (0.70V), dichromate ion(1.23V), and hydrogen peroxide (1.78V) oxidants:

Two moles of thiol coupled by one mole of iodine

| $I_2 + 2e^-$ | $\rightarrow$ | $2I^-$ |
|---|---|---|
| $2R\text{-}SH$ | $\rightarrow$ | $R\text{—}S\text{—}S\text{—}R + 2H^+ + 2e^-$ |
| $R\text{—}SH + I_2$ | $\rightarrow$ | $R\text{—}S\text{—}S\text{—}R + 2H^-I^-$ |

One mole of thiol coupled by one mole of ferric ion

| $2Fe^{3+} + 2e^-$ | $\rightarrow$ | $2Fe^{2-}$ |
|---|---|---|
| $2R\text{-}SH$ | $\rightarrow$ | $R\text{—}S\text{—}S\text{—}R + 2H^+ + 2e^-$ |
| $2R\text{-}SH + 2Fe^{3+}$ | $\rightarrow$ | $R\text{—}S\text{—}S\text{—}R + 2H^+ + 2Fe^{2+}$ |

Two moles of thiol coupled by one mole of oxygen

| $O_2 + 2H^+ + 2e^-$ | $\rightarrow$ | $H_2O_2$ |
|---|---|---|
| $2R\text{-}SH$ | $\rightarrow$ | $R\text{—}S\text{—}S\text{—}R + 2H^+ + 2e^-$ |
| $2R\text{-}SH + O_2$ | $\rightarrow$ | $R\text{—}S\text{—}S\text{—}R + H_2O_2$ |

Six moles of thiol coupled by one mole of dichromate ion

| $Cr_2O_7^{2-} + 14H^+ + 6e^-$ | $\rightarrow$ | $2Cr^{3-} + 7H_2O$ |
|---|---|---|
| $6R\text{-}SH$ | $\rightarrow$ | $3R\text{-}S\text{-}S\text{-}R + 6H^+ + 6e^-$ |
| $6R\text{-}SH + Cr_2O_7^{2-} + 8H^-$ | $\rightarrow$ | $3R\text{-}S\text{-}S\text{-}R + 7H_2O + 2Cr^{3+}$ |

Two moles of thiol coupled by one mole of hydrogen peroxide

| $H_2O_2 + 2H^+ + 2e^-$ | $\rightarrow$ | $2H_2O$ |
|---|---|---|
| $2R\text{-}SH$ | $\rightarrow$ | $R\text{—}S\text{—}S\text{—}R + 2H^+ + 2e^-$ |
| $2R\text{-}SH + H_2O_2$ | $\rightarrow$ | $R\text{—}S\text{—}S\text{—}R + 2H_2O$ |

The process for the formation of disulfide links in microcapsule walls and the properties of the capsule suspension (CS) product are influenced by the properties of the oxidant. For example, (1) the solubility of the oxidant in water affects the solids content of the CS produced, usually the lower the solubility the lower the resulting solids; (2) the nature of the oxidant may affect the colloidal stability of the oil-in-water emulsion during the wall forming process; (3) the number of moles of oxidant used will determine the amount of oxidant by-product in the resulting capsule suspension; (4) the nature of the oxidant will determine the nature of the by-product which may be desirable or undesirable in the capsule suspension product (for example, it may be desirable to neutralize the by-product or remove it from the capsule suspension product); (5) the type and amount of oxidant needed will influence the cost of the capsule suspension product; (6) the partition coefficient of the oxidant between the aqueous phase and the organic phase will determine the rate at which disulfide formation will occur; and (7) the nature of the oxidant(s) may permit the coupling of two or more oxidation reactions to make the use of one oxidant catalytic.

The Process.

In one embodiment of this invention, a process is described where microcapsule walls can be made at the interface of an oil-in-water emulsion by the oxidative coupling of thiols dissolved in the oil phase to form a disulfide polymer where all of the wall forming materials contain sulfur atoms.

The general procedure is as follows. An oil or organic phase is prepared comprised of the material to be encapsulated and at least a solution of a polythiol compound. The organic phase may consist of a single liquid material, or one or more active liquid materials or solid materials dissolved in an inert solvent which at most has a slight solubility to water, or may consist of a suspension of solid materials in such an organic liquid. The aqueous phase is comprised of water and a protective colloid and, optionally, where the thiol compound does not already have disulfide links, an oxidant preferably dissolved in water and capable of coupling thiols to form disulfides links prior to wall formation. An emulsion is then prepared by dispersing the organic phase into the aqueous phase employing any conventional high shear stirrer until the desired particle size is achieved. When no oxidant is present in the aqueous phase, or when oxidant in addition to that in the aqueous phase is required, an aqueous solution of oxidant may be added to the emulsion at a given temperature and the stirred mixture heated as appropriate for a further period.

The particle or droplet size of the emulsion is not critical to the invention. For greatest utility, the droplet size will be in the range of from about 0.5 to about 4,000 microns in diameter, preferably from about 1 micron to about 100 microns in diameter, most preferably from about 1 to about 25 microns in diameter. Once the desired droplet size is obtained, mild agitation is generally sufficient to prevent proper growth throughout the balance of the process.

Disulfide bonds are formed by an interfacial process as follows. The oxidant diffuses from the aqueous phase into the oil phase and oxidizes the thiol groups of the polythiol compound to disulfide groups. The partition coefficient of the oxidant usually favors its residence in the aqueous phase. The coupling reaction thus most probably takes place at or near the aqueous-organic interface. The by-products of the redox reaction diffuse back into the aqueous phase. The ratio of the number of moles of oxidant to the number of moles of thiol will determine the maximum possible number of disulfide links that can be formed.

Suitable examples of polythiol compounds include, inter alia, pentaerythritol tetra-(3-mercaptopropionate) and pentaerythritol tetra-(2-mercaptoacetate). Suitable oils include (R)-butyl 2-(4-((5trifluoromethyl)-2pyridinyl)oxy)phenoxy) propanate known as Fluazifop-p-butyl, S-ethyl di-isobutylthiocarbamate known as Butylate, and Solvesso 200. Suitable oxidants include iodine, ferric chloride, hydrogen peroxide and potassium dichromate.

A dichromate oxidation in acidic media is illustrated below in Example 1e. Protons are generated by iodine and ferric chloride oxidations of thiols resulting in a reduction in pH. Iodine and ferric chloride oxidations are illustrated in respectively Examples la and lf. In the oxidation by peroxide ($H_2O_2+2H^++2e^- \rightarrow 2H_2O$), the same number of protons are consumed as are generated by the thiol oxidation ($2R-SH \rightarrow RS-SR+2H^++2e^-$) and there is thus, in principle, no change in pH. The reaction has been examined at acidic and alkaline pH's in, respectively, Examples 1d, 1b and 1c.

In the preferred embodiment of this invention, a process is described which employs at least one polythiol compound mixed with at least one alkylated amino formaldehyde resin, where disulfide bonds and thioether bonds are formed by an interfacial reaction during microcapsule wall formation.

The general procedure is as follows. The organic phase is comprised of a solution of butylated urea formaldehyde prepolymer and a polythiol compound dissolved in an organic liquid which may constitute separately or together a solvent and an active ingredient or material to be encapsulated. The aqueous phase is comprised of water, a protective colloid and, optionally, (a) a catalyst promoting formation of thioether bonds and (b) an oxidant dissolved in water and capable of coupling thiols to disulfides. An emulsion is then prepared by dispersing the oil phase in the aqueous phase employing any conventional high shear stirrer until the desired particle size is achieved. An aqueous solution of oxidant is added to the emulsion at a given temperature and the stirred mixture is heated as appropriate for a further period.

Suitable examples of polythiol compounds include, inter alia, pentaerythritol tetra-(3-mercaptopropionate) and pentaerythritol tetra-(2-mercaptoacetate). Suitable oils include S-ethyl di-isobutylthiocarbamate known as Butylate, Solvesso 200, and solutions of chlorpryifos in Solvesso 200. Suitable oxidants include iodine, ferric chloride, hydrogen peroxide and potassium dichromate. The oxidant may be added at a temperature between 5° C. and 70° C. Preferably, the oxidant is added at a temperature between 20° C. and 50° C.

The formation of disulfide bonds by an interfacial process proceeds as described above. The ratio of the number of moles of oxidant to the number of moles of thiol will determine the maximum possible number of disulfide links that can be formed. Those thiol groups of the polythiol compound that have not been consumed in the disulfide-forming reaction may then react with the alkylated amino formaldehyde resin to form thioether bonds. The formation of thioether bonds is accelerated by acids and results in the formation of a thermoset polymer of theoretically infinite molecular weight.

The disulfide and thioether forming reactions probably occur simultaneously when the oxidation is carried out in an acidic solution, for example when using dichromate ion as the oxidant. The disulfide and thioether forming reactions probably occur sequentially when starting from a pH at or above neutrality and the redox reaction generates acid, for example when using iodine as the oxidant. The disulfide forming reaction probably occurs preferentially to the thioether forming reaction when starting from a pH at or above neutrality and the redox reaction does not alter the pH.

The rate of the thioether forming reaction will depend on the localized concentration of hydrogen ions. Protons generated by the disulfide-forming reaction will give a temporary low pH (high concentration) in the vicinity of the thiol groups of the polythiol compound. However, it is likely that the protons diffuse rapidly into the aqueous phase where they are not available to catalyze the thioether forming reaction. The rate of the reaction may be accelerated by including a catalyst such as an alkyl naphthalene sulfonic acid in the composition. The catalyst has both hydrophobic and hydrophilic segments which enables the compound to readily traverse the aqueous-organic interface. The sulfonic acid segment carries protons from the aqueous phase into the organic phase in order to promote the thioether forming reaction.

The principles of the process are illustrated by the redox reaction employing iodine or bromine. Iodine has a low solubility of 0.335 g in 1 dm$^3$ of water at 25° C., and also has an appreciable vapor pressure. This complicates the use of iodine in aqueous systems. Both difficulties are overcome by dissolving the iodine in an aqueous solution of potassium iodide. The increased solubility is due to the formation of a tri-iodide ion [$I_2+I^- \leftrightarrows I_3^-$], represented as 3I$^-$ in Table 1 above.

Without wishing to be bound by theory, when a solution of the tri-iodide is added to the aqueous phase, the tri-iodide diffuses from the aqueous phase into the emulsion droplet and oxidizes the thiol groups to disulfides at the aqueous-organic interface. The HI thus generated reduces the pH of the medium to promote the cross-linking of the alkylated amino formaldehyde resin and unreacted thiol groups. The cross-linking reaction may be enhanced by the inclusion of a catalyst and additional acid in the composition. When desired, the HI may be neutralized with $K_2CO_3$.

The amount of $KI_3$ used will determine the pH to which the system falls. On reaction with 2 moles of thiol every mole of $KI_3$ generates 2 moles of HI. The stoichiometry is important. At very high ratios of $KI_3$:SH most of the thiols will be consumed in the formation of disulfide bonds, i.e., there will be little available to cross-link the alkylated amino formaldehyde oligomers. Disulfide links are very flexible and the rigidity of the wall will be affected by concentration of such groups. The use of iodine and bromine as oxidants is illustrated by Examples 2a, 2b, 2c, 2d and 2e described below. These Experiments, done without an aminoplast resin, have shown that the reagent partitions between the aqueous and organic phases to couple thiols to disulfides between pH's of 2–8. The reagent has also been used for systems containing both thiols and an alkylated amino formaldehyde resin.

The principles of the process are further illustrated by the redox reaction employing hydrogen peroxide. Hydrogen peroxide is inexpensive and is totally soluble in water. However, with a redox potential of 1.78 volts, it is a powerful oxidizing agent and may cause colloidal destabilization of emulsions prior to wall formation. These problems may be minimized by carefully metering the reagent into an emulsion at room temperature which also helps to reduce the possibility of thermal decomposition. Excess hydrogen peroxide may be destroyed by adding an enzyme catalyst to the emulsion at room temperature and a pH of about 7. The use of hydrogen peroxide as the oxidant is illustrated in Example 2f below.

In a further embodiment of the invention a mixture of oxidants may be used to couple thiols dissolved in the oil phase to form a polymer containing disulfide linkages. The general procedure is similar to that described above with the exception that two oxidants (A) and (B) are used which may give certain benefits. For example, it may be possible to use one mole of an oxidant (A) to generate more than the number of disulfide bonds expected from the stoichiometry of the reaction between oxidant (A) and the thiols in the following manner. Following diffusion of oxidant (A) from the aqueous phase into the oil phase and oxidation of the thiol groups there to disulfide groups the reduced by-product of oxidant (A) diffuses back into the aqueous phase. If oxidant (A) is reduced by a two electron process then:

If in the aqueous phase there is a second oxidant (B) having a redox potential capable of oxidizing the reduced by-product of oxidant (A) back to its oxidized form the above cycle may be repeated.

If oxidant (B) does not itself react with the thiol groups in the oil phase, the oxidation reaction to form disulfide bonds becomes catalytic with respect to oxidant (A). This condition would pertain if the partition coefficient of oxidant (B) between the oil and water phases massively favors its residence in the aqueous phase. Such a condition may be envisaged where the oxidant (B) is an electrode immersed in the emulsion and driven by electrical power. In cases where oxidant (B) may itself react with thiol groups in the oil phase the catalytic recycle of oxidant (A) may still be possible but the efficiency of the process would be influenced by the differential between the partition coefficients of oxidants (A) and (B) between the oil and water phases.

An example of mixed oxidants include, inter alia, the use of potassium tri-iodide [oxidant (A)] and hydrogen peroxide [oxidant (B)]. Potassium trioidide is formed by reaction of iodine with potassium iodide:

Following addition of a $KI_3$ solution to the emulsion, the reagent diffuses from the aqueous phase into the organic phase and oxidizes the thiol groups to disulfide groups.

The hydrogen iodide and potassium iodide by-products diffuse back into the aqueous phase. If hydrogen peroxide is then added to the aqueous phase, it will oxide the HI to water and iodine.

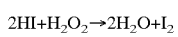

An exotherm is sometimes seen with this reaction. The iodine can recombine with potassium iodide to regenerate $KI_3$. The above mixed oxidant wall formation process is generally illustrated in FIG. 1 and may be described as follows

| Catalytic Synthesis | | |
|---|---|---|
| $KI + I_2$ | → | $KI_3$ |
| $2RSH + KI_3$ | → | R—S—S—R + 2HI + KI |
| $2RSH + H_2O_2$ | → | R—S—S—R + $2H_2O$ |
| $2HI + H_2O_2$ | → | $2H_2O + I_2$ |

As described above, hydrogen peroxide can move across the aqueous/organic interface to effect disulfide formation. Thus, there is likely to be competition between the iodine recycle and disulfide forming reactions with hydrogen peroxide. The efficiency of the recycle process will depend upon the partition coefficient of hydrogen peroxide between the aqueous and oil phases.

The process is illustrated in Example 3a using only pentaerythritol tetra-(3-mercaptopropionate), where potassium tri-iodide was added to the emulsion in sufficient quantity to cause the pH to fall from about 9.1 to 4.8, reflecting the generation of hydrogen iodide. When peroxide was post-added to regenerate iodine from HI, the pH and temperature increased and the recycle of iodine was attested by color changes in the emulsion.

The invention is further illustrated by the following examples:

Exemplification of Capsule Formation

The following examples illustrate that disulfide bonds are generated across an oil/water interface where the thiol is in the oil phase and the oxidant is dissolved in the aqueous phase. A model study was performed illustrating this interface and the generation of the disulfide bonds.

The general procedure of the model study was as follows. A solution of methyl thioglycolate (1.00 g, 9.42 mequivs) in toluene (9.00 g) was carefully layered over an aqueous solution of 9.27 g of 35.3% w/w $KI_3$ (aq) (2.0 g KI, 1.27 g $I_2$, 6 g water; $KI:I_2$ ratio of 2.4:1; 10 mequivs $I_2$). The lower aqueous phase was magnetically stirred at a speed so as to not disturb the organic/aqueous interface. After 24 hours at room temperature, both phase were still purple in color. The mixture was heated at 50° C. for three hours when all the color was lost from the upper organic layer. The mixture was then washed with 20% w/w KI (aq) and the organic layer was dried over $MgSO_4$. Analysis by GCMS (high resolution gas chromatography using a 30 m×0.25 mm×0.25 μm DB-1 column ramped from 40° C. to 300° C. at 10° C. per minute; low resolution MS in the EI+mode) showed that the only component present, other than toluene, was 3,4-dithia-1,6-hexandioic acid $(MeO_2CCH_2S)_{2-}$, m/z 210.

Examples 1a–1f (No Alkylated Amino Formaldehyde Resin Present; Various Oxidants Utilized)

Examples 1a–1f illustrate the formation of microcapsule wall compositions where all the wall forming materials contain sulfur atoms, and disulfide units are generated during wall formation. The general procedure was as follows. The organic phase was comprised of a solution of a polythiol compound. The aqueous phase was comprised of a protective colloid and, optionally, an oxidant capable of coupling thiols to form disulfides dissolved in water. An emulsion was then prepared by dispersing the organic phase in the aqueous phase employing any conventional high shear stirrer until the desired particle size was achieved. Typically, a Silverson SL2T stirrer was used at 4000–5000 rpm for between 3 and 5 minutes. An aqueous solution of oxidant was added to the emulsion at a given temperature and the stirred mixture was heated as appropriate for a further period.

Example 1a (Potassium Tri-Iodide as Oxidant)

This experiment demonstrates that microcapsules having 10 weight % walls could be made from polythiol compounds using potassium iodide as the oxidant. A solution of pentaerythritol tetra-(3-mercaptopropionate) (sold as Q43 from Evans Chemetics) (2.0 g) in Fluazifop-p-butyl [(R)-butyl 2-(4-((5trifluoromethyl)-2pyridinyl)oxy)phenoxy) propanate] (18.0 g) was emulsified in an aqueous phase of water (19.2 g) containing 40% Reax 100M (0.8 g). A solution of potassium iodide (3.2 g) and iodine (2.0 g) in water (2 ml) was added dropwise to the stirred emulsion at room temperature. Stirring was continued at room temperature for 2 hours when a solution of potassium carbonate (2.0 g) in water (2 ml) was added. Spherical microcapsules, which maintained their structure upon drying, were obtained.

Example 1b (Hydrogen Peroxide as Oxidant at Room Temperature)

This experiment demonstrated that robust microcapsules could be made from polythiol compounds using hydrogen peroxide as the oxidant at alkaline pH and ambient temperature. A solution of Q43 (2.38 g), in Solvesso 200 (12.5 g) was emulsified at high shear into an aqueous phase comprised of 40% Reax 100M (aq) (2.00 g) and distilled water (15.00 g). The emulsion was stirred at room temperature while hydrogen peroxide (2 ml 100 vol.) was added in 0.5 ml portions at 30 minute intervals, with an extra hour of stirring upon completion of addition. The pH fell from 9.1 to 7.6. The microcapsules produced before cooking were smooth, spherical, moderately strong, with no leakage on drying and were resuspendable with the same drying characteristics. The emulsion was then cooked for a total of 3 hours at 53° C. when the pH fell from 7.6 to 4.3. The drop in pH, magnified when the temperature was increased, was believed to be associated with the thermal decomposition of peroxide. After cooking, the microcapsules appeared slightly stronger.

Example 1c (Hydrogen Peroxide as Oxidant)

This experiment demonstrated that microcapsules having 10 weight % walls could be made from polythiol compounds using hydrogen peroxide as the oxidant at nearly neutral pH. A solution of pentaerythritol tetra-(2-mercaptoacetate) (2.11 g) in Solvesso 200 (11.4 g) and ethyl acetate (2.00 g) was emulsified at high shear into an aqueous phase comprised of 40% Reax 100M (2.00 g) and distilled water (15.00 g). The pH was reduced to 8 by sulfuric acid addition. The emulsion was stirred at 50° C. while 2 ml 100 vol. $H_2O_2$ was added in 0.5 ml portions at 30 minute intervals. The microcapsules produced were smooth and spherical with moderately robust walls.

Example 1d (Hydrogen Peroxide as Oxidant at Low pH)

This experiment demonstrated that moderately robust microcapsules could be made from a polythiol compound using hydrogen peroxide as the oxidant at low pH and ambient temperature. A solution of Q43 (2.3 g), in Solvesso200 (12.6 g) was emulsified at high shear into an aqueous phase of 40% Reax 100M (aq) (0.75 g), and deionized water (15.5 g). The pH was reduced from 9.5 to 2 by sulfuric acid addition. The emulsion was stirred at room temperature while hydrogen peroxide (2 ml 100 vol.) was added in 0.5 ml portions at 30 minute intervals. The emulsion was heated for 3 hours at 53° C. and then neutralized by addition of 2% $NaHCO_3$ (aq). The microcapsules produced were smooth, spherical, and moderately strong.

Example 1e (Potassium Dichromate as Oxidant)

This experiment demonstrated that microcapsules having 8 weight % walls could be made from polythiol compounds using potassium dichromate as the oxidant. A solution of Q43 (1.35 g) in Solvesso 200 (15.3 g) was emulsified at high shear into an aqueous phase consisting of 40% Reax 100M (aq) (2.35 g) and distilled water (17.65 g). The emulsion was stirred at 35° C. while 0.5N $K_2Cr_2O_7$ (7.3 g, held at 35° C. to maintain solubility) was added in 1.5 ml portions at 15 minute intervals along with 5.1 ml c.HCl at 1 ml per 15 minutes (pH 1 after 2.5 hours). The emulsion was heated for a total of 2.5 hours. The microcapsules produced were spherical and strong, with no leakage on drying and were resuspendable in water.

Example 1f (Ferric Chloride as Oxidant)

This experiment demonstrated that microcapsules having 8 weight % walls could be made from polythiol compounds using ferric chloride as the oxidant. A solution of Q43 (1.35 g) in Solvesso 200 (15.3 g) was emulsified at high shear into an aqueous phase comprised of Lomar D (0.94 g), distilled water (11.06 g), and ~8 g saturated $FeCl_3$ solution (from 10 ml of 10% w/w). The emulsion was then stirred at 50° C. while 2×5 g further washings of the remaining $FeCl_3$ were added at hourly intervals (pH 0.5 after 3 hours). The emulsion was heated for a total of 3 hours. The microcapsules produced were spherical and moderately strong, with no leakage on drying and were resuspendable in water.

Examples 2a–2f (Thiol Compounds and Alkylated Amino Formaldehyde Resin Present; Various Oxidants)

Examples 2a–2f illustrate the formation of microcapsule wall compositions where some of the wall forming materials contain sulfur atoms and some do not, and disulfide units are generated during wall formation. The general procedure was as follows. The organic phase was comprised of a solution of butylated urea formaldehyde prepolymer and a polythiol compound. The aqueous phase was comprised of a protective colloid and, optionally, a catalyst promoting formation of thioether bonds dissolved in water. An emulsion was then prepared by dispersing the organic phase into the aqueous phase employing any conventional high shear stirrer until the desired particle size was achieved. A solution of oxidant in water was added to the oil-in-water emulsion at a temperature between 20° C. and 55° C. at pH≧8. The pH fell to a value dependent upon the ratio of thiol groups to the nature and amount of the oxidant. The integrity of the microcapsule walls was assessed by microscopic visual inspection. Where appropriate, the pH was further reduced to about 2 by the addition of sulfuric acid and the mixture heated at 50° C.±50° C. for a given period.

Example 2a ($KI_3$ as Oxidant)

This experiment demonstrated that when using a mole ratio of 9.6:1 of thiol: iodine, the pH reduced from about 9.5 to about 4.1 and poor quality walls were formed. When the pH of the emulsion was further reduced to about 1.7 by addition of $H_2SO_4$, good quality walls were formed. This suggested that, at the above mole ratio, insufficient disulfide links were formed to produce integral walls, and that robust walls were subsequently formed by formation of thioether bonds between the polythiol compound and prepolymer at low pH. A solution of Q43 (0.70 g) and etherified urea formaldehyde resin (sold as Beetle-80 from Cytec) (1.60 g) in Aromatic 200 (12.5 g) was emulsified at high shear into an aqueous-phase comprised of 40% Reax 100M (0.75 g) and PetroBAF (alkylnaphthalene sulfonic acid sodium salt from Witco) (0.03 g) in distilled water (13.5 g) at room temperature. The pH of the emulsion was about 9. A solution of iodine (0.038 g) and potassium iodide (0.060 g) in water (1.8 ml) was added dropwise to the emulsion at room temperature. The pH fell to 4.1. Examination by light microscopy showed that weak walls had formed. The pH of the formulation was reduced to 1.7 by the addition of sulfuric acid and the mixture was heated to 50° C.±5° C. for 2 hours. The microcapsules produced had smooth spherical strong walls which did not leak on drying and, after drying, were re-suspendable in water.

Example 2b ($KI_3$ oxidant)

This experiment and the result was similar to that described for Example 2a with the exception that pentaerythritol tetra-(2-mercaptoacetate) was substituted for Q43. A solution of pentaerythritol tetra-(2-mercaptoacetate) (0.70 g) and Beetle 80 (1.60 g) in Aromatic 200 (12.6 g) was emulsified at high shear into an aqueous phase comprised of 40% Reax 100M (0.75 g) and PetroBAF (0.03 g) in distilled water (15.5 g) at room temperature. The pH of the emulsion was about 9. A solution of iodine (0.038 g) and potassium iodide (0.060 g) in water (1.8 ml) was added dropwise to the emulsion at room temperature. The pH fell to 4.2. Examination by light microscopy showed that weak walls had formed. The pH of the formulation was reduced to 1.7 by the addition of sulfuric acid, and the mixture was heated to 50° C.±5° C. for 2 hours. The microcapsules produced had smooth spherical strong walls which did not leak on drying and, after drying, were resuspendable in water.

Example 2c ($KI_3$ as Oxidant)

This experiment demonstrated that when using a mole ratio of 5.4:1 of thiol: iodine, the pH fell from about 9.5 to about 2.4 and reasonable quality walls were formed, probably reflecting the formation of both disulfide and thioether groups. When the pH of the emulsion was further reduced to about 1.9 by addition of $H_2SO_4$, good quality walls were formed in the absence of a catalyst for the formation of thioether bonds. A solution of pentaerythritol tetra-(2-mercaptoacetate) (0.70 g) and Beetle 80 (1.60 g) in Aromatic 200 (14.9 g) was emulsified at high shear into an aqueous phase comprised of 40% Reax 100M (0.75 g) in distilled water (15.5 g) at room temperature. The pH of the emulsion was about 9. A solution of iodine (0.076 g) and potassium iodide (0.120 g) in water (3.6 ml) was added dropwise to the emulsion at room temperature. The pH fell to 2.4. Examination by light microscopy showed that reasonably strong walls had formed. The pH of the formulation was reduced to 1.9 by the addition of sulfuric acid and the mixture was heated to 50° C.±5° C. for 2 hours. The microcapsules produced had smooth spherical strong walls which did not leak on drying and, after drying, were resuspendable in water.

Example 2d ($KI_3$ oxidant)

This experiment was similar to that described for Example 2c with the exception that a catalyst for the formation of thioether bonds was included in the aqueous phase. At pH 2.4, reasonable quality walls were formed. When the pH of the emulsion was further reduced to about 1.9 by addition of $H_2SO_4$, very good quality walls were formed. A solution of pentaerythritol tetra-(2-mercaptoacetate) (0.70 g) and Beetle 80 (1.60 g) in Aromatic 200 (14.9 g) was emulsified at high shear into an aqueous phase comprised of 40% Reax 100M (0.75 g) and PetroBAF (0.03 g) in distilled water (15.5 g) at room temperature. The pH of the emulsion was about 9. A solution of iodine (0.076 g) and potassium iodide (0.120 g) in water (3.6 ml) was added dropwise to the emulsion at room temperature. The pH fell to 2.4. Examination by light microscopy showed that reasonably strong walls had formed. The pH of the formulation was reduced to 1.9 by the addition of sulfuric acid and the mixture was heated to 50° C.±5° C. for 2 hours. The microcapsules produced had smooth spherical very strong walls which did not leak on drying and, after drying, were resuspendable in water.

Example 2e (KBr, $Br_2$ as Oxidant)

This experiment demonstrates that bromine can be used in the same manner described above for iodine. A solution of Q43 (0.7 g) and Beetle 80 resin (1.6 g) in Solvesse200 (12.6 g) was emulsified at high shear into an aqueous phase comprised of 40% Reax 100M (aq) (0.75 g), PetroBAF (30 mg) and water (15.5 g). The emulsion was stirred at room temperature while 5% w/w $KBr_3$ (aq) (1.7 g with $KBr:Br_2$ ratio 2.4:1 molar) was added when the pH fell to 1.8. On completion of addition, the emulsion was heated at 50° C.

for 5 hours at pH 1.8. The emulsion was then neutralized by addition of 5% $K_2CO_3$ (aq). The microcapsules produced were smooth, spherical, strong, with no leakage on drying, and were resuspendable with the same drying characteristics.

Example 2f (Hydrogen Peroxide as Oxidant)

This experiment demonstrates that disulfide and thioether linkages could be made sequentially using, respectively, hydrogen peroxide as the oxidant, and acid catalysis in microcapsules employing an alkylated amino formaldehyde resin and pentaerythritol tetra-(3-mercaptopropionate). A solution of Q43 (2.3 g) and Beetle 80 resin (2.3 g) in Solvesso 200 (10.2 g) was emulsified at high shear into an aquesous phased comprised of 40% Reax 100M (1.13 g), PetroBAF (45 mg), and distilled water (16.0 g). The emulsion at pH 9.3 was stirred at room temperature while $H_2O_2$ (100 Vol, 4 ml) was added in one ml aliquots at thirty minute intervals. The temperature after the first addition rose from 19° C. to 21° C., and then stayed at 20° C. throughout the remaining additions. The color remained creamy white. The pH reduced to 8.3, 7.3, 6.8 and 6.6, respectively, after each of the four additions. Examination by light microscopy indicated that weak walls had been formed. Thirty minutes after peroxide addition the pH was reduced to 1.9 by using $H_2SO_4$, and the emulsion heated to 50° C. for three hours giving good quality microcapsules.

Example 3a (The Use of Mixed Oxidants)

The following example illustrates the formation of microcapsule wall compositions containing disulfide units using mixed oxidants. The wall forming materials may all contain sulfur atoms, or some materials may contain sulfur atoms and some might not.

Example 3a (Potassium Tri-Iodide and Hydrogen Peroxide as Oxidants)

This experiment demonstrates that microcapsules can be made from Q43 using a mixture of oxidizing reagents where potassium tri-iodide was regenerated by hydrogen peroxide. A solution of Q43 (2.3 g) in Solvesso 200 (12.5 g) was emulsified at high shear into an aqueous phase comprised of 40% Reax 100M (aq) (2.00 g) and distilled water (14.25 g). The emulsion was stirred at room temperature while 5.4 g of 5.2% w/w $KI_3$ (aq) ($KI:I_2$ ratio 2.4:1 molar) was added dropwise. After stirring for 2 hours at room temperature the pH fell from 9.1 to 4.8. The color of the mixture became pale brown. Hydrogen peroxide (2 ml 100 vol) was then added at room temperature in 1 ml portions at 1 hour intervals, followed by an extra half hour of stirring on completion of addition. After each peroxide addition, the temperature increase from about 18° C. to about 21° C. and the pale brown color was replaced by an orange color. The temperature fell back to about 18° C. and the color reverted to pale brown after some time. The pH after the first peroxide addition increased to about 6.0. The pH, temperature and color changes were believed to reflect the regeneration of iodine and hence potassium tri-iodide after each peroxide addition. After standing overnight, the pH dropped to 4.0 and the orange color disappeared. The microcapsules produced before peroxide addition were smooth and spherical, but were weak and burst on drying. After peroxide addition the microcapsules were smooth, spherical with no leakage on drying and were resuspendable with the same drying characteristics.

Example 4a (The Use of Preformed Disulfides)

The following example illustrates the formation of microcapsule wall compositions containing disulfide units wherein the disulfide unit is already present in the starting material. The wall forming materials may all contain sulfur atoms, or some materials may contain sulfur atoms and some may not.

Example 4a (2-hydroxyethyl Disulfide as Cross-Linker)

This experiment demonstrates that microcapsules could be made from an alkylated amino formaldehyde resin and 2-hydroxyethyl disulfide, i.e., the disulfide unit is already present in the starting material and hydroxyl groups of 2-hydroxyethyl disulfide react with the resin. A solution of 2-hydroxyethyl disulfide (0.70 g) and Beetle 80 (1.60 g) in Solvesso 200 (12.6 g) was emulsified at high shear into an aqueous phase comprised of 40% Reax 100M (aq) (0.75 g), PetroBAF (0.04 g), and deionised water (15.5 g). The pH was reduced to 1.9 by $H_2SO4$ addition. The emulsion was heated for 6 hours at 50° C., and then neutralized by addition of 2% $NaHCO_3$ (aq). The microcapsules produced were spherical and moderately strong.

Exemplification of Formation of Capsule Suspensions With an Active Ingredient Preparation of Microcapsules A suspension of microcapsules containing as a pesticide either the insecticides chlorpyrifos or lambda-cyhalothrin or the herbicide butylate was prepared utilizing the microencapsulation process described herein wherein the pesticide was encapsulated within the polymeric shell wall formed by oxidative coupling of a polythiol compound or a combination of oxidative coupling and interfacial polymerization and condensation of a mixture of a polythiol compound and a butylated urea formaldehyde prepolymer. While the examples provided below exemplify a single encapsulated pesticide, it should be easily recognized by one skilled in the art that the present invention is not limited to a single encapsulated ingredient, but may contain any number and combination of ingredients, such as two insecticides and a herbicide to the extent that they are chemically compatible.

The general procedure was as follows. The organic phase was comprised of the pesticide, which in some cases was dissolved in a solvent, at least one polythiol compound and, optionally, a butylated urea formaldehyde prepolymer. The aqueous phase was comprised of a protective colloid and, in many cases, an emulsifier/phase transfer catalyst dissolved in water. An emulsion is then prepared by dispersing the organic phase in the aqueous phase employing any conventional high shear stirrer until the desired particle size is achieved. An aqueous solution of oxidant is added to the oil-in-water emulsion at room temperature. The mixture is stirred for 3 hours at room temperature, and then heated to 50° C.±5° C. for 3 hours. The resulting capsule suspension is removed from the heat and post-formulated with a biocide, suspending agents, and aqueous solution of base, to raise the pH to 5.5, using a conventional high shear stirrer.

Compositions were prepared according to the foregoing procedure including ingredients as listed below:

TABLE 3

| Ingredients | Example #: 5 Weight (g) | 6 Weight (g) | 7 Weight (g) | 8 Weight (g) | 9 Weight (g) | 10 Weight (g) |
|---|---|---|---|---|---|---|
| Butylate (technical grade) | 18.00 | 18.00 | 17.99 | 18.02 | 18.02 | 18.01 |
| Beetle 80 (butylated urea-formaldehyde resin from Cytec) | 0.42 | 0.43 | 0.40 | 1.02 | 1.41 | n.a. |
| Q43 (pentaerythritol tetra-(3-mercaptoproprionate) from Evans Chemetics) | 1.64 | 1.66 | 1.59 | 1.00 | 0.62 | 2.02 |
| Kraftsperse 25M (lignosulfonic acid, sodium salt protective colloid from WestVaco) | 1.048 | 1.051 | 1.05 | 1.057 | 1.049 | 1.052 |
| PetroBAF (alkylnapthalene sodium salt surfactant from Witco) | 0.009 | 0.009 | 0.009 | 0.013 | 0.022 | 0.010 |
| Water | 33.11 | 30.58 | 31.79 | 28.54 | 27.60 | 36.02 |
| Potassium Iodide | 1.53 | 0.85 | 1.16 | 0.53 | 0.34 | 1.72 |
| Iodine | 1.52 | 0.85 | 1.18 | 0.52 | 0.33 | 1.71 |
| Potassium Carbonate | 0.80 | 0.453 | 0.623 | 0.282 | 0.174 | 0.904 |
| Proxel GXL (biocide based on a 20% solution of 1,2-Benzisothiazolin-3-one in dipropylene glycol from Avecia) | 0.1 | 0.1 | 0.1 | 0.1 | 0.1 | 0.1 |
| Kelzan (xanthan gum from Kelco) | n.a. | 0.30 | 0.030 | 0.032 | 0.031 | 0.030 |
| Attagel 40 (attapulgite clay from Englehard) | n.a. | 0.303 | 0.300 | 0.310 | 00304 | .0300 |
| Median Particle Size ($\mu$m) | 9.5 | 8.9 | 10.2 | 8.2 | 8.6 | 13.6 |
| % Q43* | 80 | 80 | 80 | 50 | 30 | 100 |
| % $KI_3$# | 90 | 50 | 70 | 50 | 50 | 100 |

*Percentage with respect to total wall content.
Stoichiometric percentage with respect to sulfhydryl groups.

TABLE 4

| Ingredients | Example #: 11 Weight (g) | 12 Weight (g) | 13 Weight (g) | 14 Weight (g) |
|---|---|---|---|---|
| Butylate (technical grade) | 17.98 | n.a. | n.a. | n.a. |
| Chlorpyrifos (technical grade) | n.a. | 11.7 | 11.70 | n.a. |
| Lambda-Cyhalothrin (technical grade) | n.a. | n.a. | n.a. | 9.01 |
| Aromatic 200 (solvent from Exxon) | n.a. | 6.30 | 6.30 | 9.00 |
| Beetle 80 | 0.39 | 0.42 | 0.39 | 0.39 |
| Q43 | 1.60 | 1.58 | 1.70 | 1.60 |
| Kraftsperse 25M | 1.054 | n.a. | n.a. | n.a. |
| Reax 100M (protective colloid, 40% solution, from WestVaco) | n.a. | 2.02 | 2.01 | 2.01 |
| Water | 33.40 | 25.14 | 26.17 | 25.01 |
| Potassium Iodide | 1.49 | 1.77 | 1.76 | 1.76 |
| Iodine | 1.51 | 1.75 | 1.75 | 1.75 |
| Potassium Carbonate | 0.801 | 0.954 | 0.954 | 0.951 |
| Proxel GXL | 0.1 | 0.1 | 0.1 | 0.1 |
| Kelzan, | n.a. | 0.03 | 0.035 | 0.03 |
| Attagel 40 | n.a. | 0.300 | 0.302 | 0.300 |
| Median Particle Size ($\mu$m) | 11.5 | 10.7 | 9.6 | 9.2 |
| % Q43* | 80 | 80 | 80 | 80 |
| % $KI_3$# | 90 | 110 | 110 | 110 |

*Percentage with respect to total wall content.
Stoichiometric percentage with respect to sulfhydryl groups.

Compositions were prepared according to the foregoing general procedure with the following exception—after addition of an aqueous solution of the oxidant to the oil in water emulsion at room temperature, the mixture was immediately heated to 50° C.±5° C. for 3 hours. Composition ingredients are listed below:

TABLE 5

| Ingredients | Example #: 15 Weight (g) | 16 Weight (g) | 17 Weight (g) | 18 Weight (g) | 19 Weight (g) | 20 Weight (g) | 21 Weight (g) | 22 Weight (g) |
|---|---|---|---|---|---|---|---|---|
| Butylate (technical grade) | 18.02 | 18.00 | 18.05 | 18.00 | 18.01 | 18.01 | | |
| Chlorpyrifos (technical grade) | n.a. | n.a. | n.a. | n.a. | n.a. | n.a. | 11.60 | 11.60 |
| Aromatic 200 | n.a. | n.a. | n.a. | n.a. | n.a. | n.a. | 6.32 | 6.31 |
| Beetle 80 | 0.42 | 0.43 | 0.40 | 1.03 | 1.42 | n.a. | 0.41 | 0.39 |

TABLE 5-continued

| Ingredients | 15 Weight (g) | 16 Weight (g) | 17 Weight (g) | 18 Weight (g) | 19 Weight (g) | 20 Weight (g) | 21 Weight (g) | 22 Weight (g) |
|---|---|---|---|---|---|---|---|---|
| Q43 | 1.64 | 1.65 | 1.60 | 1.02 | 0.61 | 2.02 | 1.61 | 1.59 |
| Kraftsperse 25M | 1.049 | 1.052 | 1.065 | 1.064 | 1.049 | 1.06 | 1.05 | 1.07 |
| PetroBAf | 0.009 | 0.009 | 0.010 | 0.013 | 0.020 | 0.010 | 0.009 | 0.009 |
| Water | 28.57 | 30.55 | 31.82 | 28.57 | 27.64 | 36.01 | 30.58 | 33.10 |
| Potassium Iodide | 1.50 | 0.85 | 1.18 | 0.52 | 0.32 | 1.72 | 0.83 | 1.51 |
| Iodine | 1.49 | 0.85 | 1.16 | 0.53 | 0.32 | 1.74 | 0.85 | 1.50 |
| Potassium Carbonate | 0.808 | 0.451 | 0.622 | 0.284 | 0.173 | 0.905 | 0.45 | 0.801 |
| ProxelGXL | 0.1 | 0.1 | 0.1 | 0.1 | 0.1 | 0.1 | 0.1 | 0.1 |
| Kelzan | n.a. | 0.033 | 0.033 | 0.031 | 0.032 | 0.032 | 0.031 | 0.030 |
| Attagel 40 | n.a. | 0.303 | 0.300 | .0300 | 0.300 | 0.300 | 0.304 | 0.302 |
| Median Particle Size (μm) | 9.8 | 8.3 | 10.0 | 9.7 | 8.0 | 11.3 | 10.0 | 11.8 |
| % Q43* | 80 | 80 | 80 | 50 | 30 | 100 | 80 | 80 |
| % KI$_3$# | 90 | 50 | 70 | 50 | 50 | 100 | 50 | 90 |

*Percentage with respect to total wall content.
Stoichiometric percentage with respect to sulfhydryl groups.

Preparation of Standard Aminoplast Samples (Having No Preformed Disulfide Linkages or Oxidation Step to Form Disulfide Linkages)

Additionally, the following standard aminoplast samples were prepared as standards for comparison against the above examples. The wall forming materials contain no preformed disulfide linkages nor does the process contain a step for the (oxidative) formation of disulfide linkages. The standard aminoplast samples were prepared according to the foregoing general procedure with the following exceptions: (1) an acidifying agent was added to the aqueous phase in order to reduce the pH to 2, (2) the addition of an aqueous solution of oxidant was omitted, and (3) the resulting oil-in-water emulsion was immediately heated to 50° C.±5° C. for 3 hours. Comprehensive process procedures are described in U.S. Pat. Nos. 4,956,129, 5,160,529 and 5,332,584. Composition ingredients are listed below:

| Ingredients | Weight (g) | Weight (g) |
|---|---|---|
| Butylate (technical grade) | 19.35 | n.a. |
| Chlorpyrifos (technical grade) | n.a. | 17.79 |
| Aromatic 200 | n.a. | 9.58 |
| Beetle 80 | 1.95 | 3.85 |
| Q43 | 0.22 | 0.99 |
| Reax 100M (40% solution) | 2.265 | n.a. |
| Reax 83A (protective colloid from WestVaco) | n.a. | .82 |
| PetroBAF | 0.026 | 0.029 |
| Sulfuric Acid (50% solution) | 0.20 | 0.40 |
| Water | 20.24 | 26.29 |
| Proxel GXL | 0.1 | 0.1 |
| Kelzan | 0.030 | 0.061 |
| Attagel 40 | 0.300 | 0.60 |
| Median particle size (μm) | 8.7 | 9.4 |
| % Q43* | 10 | 20 |
| % KI$_3$# | 0 | 0 |

*percentage with respect to total wall content
stoichiometric percentage with respect to sulfhydryl groups In vitro Release Rate Evaluation The compositions of Examples 5–11 and 15–20 were tested in vitro for release rate in presence of water and, in some cases, the presence of base. Untreated samples were treated as follows. The equivalent of 0.1 g a.i. of butylate capsule suspension (CS) was diluted with 1.5 ml water, vacuum filtered on a 0.8 micron filter paper, and placed in a desiccator for approximately one hour prior to performing release rate measurements.

Base-treated samples were treated as follows. The equivalent of 0.1 g a.i. of butylate CS was diluted with either 3 ml of 0.1 M KOH (pH 12.5) or 30 ml of 10 mM KOH solution (pH 11.6). The sample was rolled for 6 hours, vacuum filtered on a 0.8 micron filter paper, and placed in a dessicater for approximately one hour prior to performing release rate measurements.

Release rate studies were conducted employing a Cahn RH electrobalance to monitor the rate of evaporative weight loss of butylate from the microcapsules under vacuum. Samples were removed from the desiccator and the excess filter paper trimmed to fit the sample pan of the electrobalance. The samples were placed on the sample pan and allowed to equilibrate at 40° C. for 10 minutes before placing under vacuum. The weight loss due to butylate, measured with the electrobalance enclosed under vacuum, was recorded on a chart recorder.

Referring to Table 6 below, the data in column 4 demonstrates that the diffusion controlled rate of release of encapsulated a.i. can be adjusted by modifying (1) the amount of the cross-linker Q43, (2) the amount of the oxidant added to form disulfide linkages, and (3) to a lesser extent, the process conditions. The data in columns 5 and 6 demonstrate that the disulfide bonds can be cleaved under alkaline conditions resulting in a faster release of encapsulated a.i. relative to non-triggered diffusion controlled conditions (column 4). As shown in Table 6, the standard aminoplast microcapsule formulation does not contain disulfide linkages and therefore does not break down under the alkaline conditions given below.

TABLE 6

Release Rate Data

| Example # | % Q43* | % KI₃# | Release Rate (mg/min) neutral - water | Release Rate (mg/min) alkaline - 0.1M KOH | Release Rate (mg/min) alkaline - 10 mM KOH |
|---|---|---|---|---|---|
| Standard Aminoplast | 10 | 0 | 3.3 ± 0.6 | 0.2 | 1.8 |
| 5 | 80 | 90 | 17.4 ± 2.0 | — | — |
| 6 | 80 | 50 | 0.0 (2 trials) | 5.3 | 0.9 |
| 7 | 80 | 70 | 17.8 | — | — |
| 8 | 50 | 50 | 4.6 ± 1.0 | 9.1 | 10.7 |
| 9 | 30 | 50 | 5.4 ± 0.8 | 12.3 | 7.2 |
| 10 | 100 | 100 | 16.4 ± 0.6 | — | — |
| 11 | 80 | 90 | 13.5 ± 2.2 | — | — |
| 15 | 80 | 90 | 16.8 ± 1.8 | — | — |
| 16 | 80 | 50 | 0.0 (3 trials) | 5.6 | 1.0 ± 0.6 |
| 17 | 80 | 70 | 14.2 ± 2.6 | — | — |
| 18 | 50 | 50 | 0.0 (2 trials) | 7.5 | 3.6 |
| 19 | 30 | 50 | 2.7 | 9.6 | 3.2 |
| 20 | 100 | 100 | 7.4 ± 0.2 | 11.2 | — |

*Percentage with respect to total wall content.
Stoichiometric percentage with respect to sulfhydryl groups.

Biological Evaluation

The compositions of Examples 12, 13, 21 and 22 were tested for biological activity the following species: *Lygus hesperus* (a sucking pest), and either *Helicoverpa zea* or *Heliothis virescens* (foliar feeding lepidoptera with alkaline guts).

Test 1

A. Contact/Residue Contact (Species: *Lygus hesperus*)

The test procedure was as follows. Cardboard cages containing a fresh green bean were infested with 10 adult bugs. Four replicates per rate were sprayed in the Potter Tower at 250 liters/hectare. Materials were dissolved in 0.05% X-77 in water. Previous test results produced an LC50 of ~220ppm for Lorsban 4E, so rates of 600, 400, 267, and 178 ppm were chosen for it. Results for CS formulations have frequently produced LC50s much higher at the start of the test, so rates of 2700, 1800. 1200, 800, 533 ppm were chosen for them. Morality assessments were made at 1, 2, 3, 4, 5, and 6 DAT.

The LC50s in ppm are given in Table 7:

TABLE 7

| Formulation | 1DAT | 2DAT | 3DAT | 4DAT | 5DAT | 6DAT |
|---|---|---|---|---|---|---|
| Lorsban 4E* | 262 | 253 | 252 | 258 | 260 | 257 |
| Example 13 | 2118 | 1433 | 1245 | 1253 | 1218 | 1199 |

*Chlorpyrifos emulsion concentrate produced by Dow Chemical containing 4 pounds chlorpyrifos per gallon This experiment demonstrates that the microcapsules exhibit good barrier properties, thus providing improved beneficial (non-foliar feeding) insect protection with respect to the standard, Lorsban 4E. The decrease in LC50 values over time in Example 13 is due to the slow diffusion controlled release of the encapsulated chlorpyrifos.

B. Foliar Persistence (Species: *Heliothis virescens*)

The test procedure was as follows. Cotton plants were sprayed in the track sprayer at 250 liters/hectare. Previous tests produced LC50s of ~75 ppm for Lorsban 4E against Heliothis, so rates of 200, 100, 50, and 25 ppm were chosen for all formulations. Plants were treated on two consecutive days, four rates per formulation, with the first day's treatments kept in the glasshouse. On the second day, after the final treatment, treated leaves were detached for infestation. Three replicates of 20 insects per replicate were infested. Mortality assessments were made 2 days after infesting.

The LC50s in ppm are given in Table 8:

TABLE 8

| Formulation | 0DAT | 2DAT |
|---|---|---|
| Lorsban 4E | 104 | — |
| Example 13 | 58 | 120 |

— indicates no LC50 calculated due to insufficient data

This experiment demonstrates that the disulfide bonds of the microcapsule wall are being cleaved within the gut of the insect resulting in comparable insect control to the standard, Lorsban 4E.

Test 2

A. Contact/Residue Contact (Species: *Lygus hesperus*)

The test procedure was as follows. Adult bugs in cages were sprayed at 250 l/h. There were four replicates of 10 insects for 5 rates of each formulation. Mortality assessments were made at 1, 2, 3, 4, 5, and 6 DAT.

The LC50s in ppm are given in Table 9:

TABLE 9

| Formulation | 1DAT | 2DAT | 3DAT | 4DAT | 5DAT | 6DAT |
|---|---|---|---|---|---|---|
| chlorpyrifos technical | 313 | 310 | 311 | 313 | 313 | 325 |
| Example 13 | 2209 | 1158 | 986 | 836 | 689 | 650 |

This experiment demonstrates that the microcapsules of the present invention exhibit good barrier properties, thus providing improved beneficial insect protection with respect to the standard, chlorpyrifos technical. The decrease in LC50 values over time in Example 13 is due to the slow diffusion controlled release of the encapsulated chlorpyrifos.

B. Foliar Persistence (Species: *Helicoverpa zea*)

The test procedure was as follows. *Helicoverpa zea* was the subject of the Lepidoptera First Instar Foliar method. Detached cotton leaves were sprayed at 250 l/h in the Potter Tower. Neonate larvae were infested on disks of treated leaves. There were three replicates of 18 insects for 3 rates of each formulation. Mortality assessments were made at 1, 2, and 3 DAT. The LC50s in ppm are given in Table 10:

TABLE 10

| Formulation | 1DAT | 2DAT | 3DAT |
| --- | --- | --- | --- |
| chlorpyrifos technical | 9.8 | 8.6 | 12.2 |
| Example 13 | 13.9 | 12.8 | 11.1 |

This experiment demonstrates that the disulfide bonds of the microcapsule wall are being cleaved within the gut of the insect resulting in comparable insect control to the standard, chlopyrifos technical.

Test 3

Foliar Persistence (Species: *Helicoverpa zea*)

The test procedure was as follows. *Helicoverpa zea* was the subject of the Lepidoptera First Instar Foliar method. Detached cotton leaves were sprayed at 250 l/h in the Potter Tower. Neonate larvae were infested on disks of treated leaves. There were four replicates of 15 insects for three rates of each formulation. Mortality assessments were made at 2 DAT. The LC50s in ppm are given in Table 11.

TABLE 11

| Formulation | % Q43 | % KI$_3$ | LC50 | Comments |
| --- | --- | --- | --- | --- |
| Lorsban 4E | 0 | 0 | 14.5 | Standard - emulsifiable concentrate |
| Chlorpyrifos CS | 10 | 0 | 96.4 | Standard - aminoplast microcapsule |
| Example 12 | 80 | 110 | 8.4 | >90% disulfide linkages |
| Example 13 | 80 | 110 | 14.7 | >90% disulfide linkages |
| Example 21 | 80 | 50 | 17.2 | 50% disulfide linkages |
| Example 22 | 80 | 90 | 14.3 | 90% disulfide linkages |

This experiment demonstrates that the disulfide bonds of the microcapsule wall are being cleaved within the gut of the insect resulting in comparable insect control to the standard, Lorsban 4E. The standard aminoplast formulation does not contain disulfide linkages and therefore was not expected to breakdown in the gut of the insect, as is reflected by its LC50 value.

Although this invention has been described with respect to specific embodiments, the details hereof are not to be construed as limitations, for it will be apparent that various, equivalents, changes and modifications may be resorted to without parting from the spirit and scope of the invention, and it is understood that such equivalent embodiments are intended to be included within the scope of the invention.

What is claimed is:

1. A microcapsule comprising a liquid core material which is substantially insoluble in water and enclosed within a solid permeable shell of a polymer resin containing disulfide linkages.

2. A microcapsule capable of a variable rate of release of an encapsulated liquid core material, wherein the microcapsule comprises a liquid core material which is substantially insoluble in water encapsulated within a solid permeable shell of a polymer resin comprising one or more disulfide linkages, wherein the liquid core material comprises one or more pesticides; wherein the liquid core material is gradually released by diffusion through the solid permeable shell in a first environment that does not cleave the disulfide linkages; and wherein the liquid core material is quickly released in a second environment that cleaves the disulfide linkages.

3. A microcapsule according to claim 2 wherein at least one of the insecticides is a pyrethroid.

4. A microcapsule according to claim 3 wherein the pyrethroid is lambda cyhalothrin.

5. A microcapsule according to claim 2 wherein at least one of the insecticides is an organophosphorus insecticide.

6. A microcapsule according to claim 5 wherein the organophosphorus insecticide is chlorpyrifos.

7. A microcapsule according to claim 1 wherein the pesticide is at least one or more herbicides.

8. A microcapsule according to claim 7 wherein at least one of the herbicides is butylate.

9. A microcapsule according to claim 1 wherein the liquid core material comprises a solid pesticide dissolved within a solvent.

10. A microcapsule according to claim 1 wherein the liquid core material is further comprised of a solid ultraviolet protectant dispersed throughout the liquid core.

11. The microcapsule of claim 2, wherein the median particle size of the microcapsule is from 8.0 μm to 13.6 μm.

* * * * *